United States Patent [19]

Yamada et al.

[11] Patent Number: 5,287,750
[45] Date of Patent: * Feb. 22, 1994

[54] APPARATUS FOR INSPECTING MECHANICAL STRENGTH OF BOTTOM PORTIONS OF BOTTOM-CLOSED HOLLOW PIPES

[75] Inventors: Satoru Yamada; Koji Tanaka, both of Nagoya, Japan

[73] Assignee: NGK Insulators, Ltd., Japan

[*] Notice: The portion of the term of this patent subsequent to Mar. 30, 2000 has been disclaimed.

[21] Appl. No.: 956,388

[22] Filed: Oct. 5, 1992

Related U.S. Application Data

[63] Continuation of Ser. No. 685,144, Apr. 15, 1991, Pat. No. 5,197,335.

[30] Foreign Application Priority Data

Apr. 21, 1990 [JP] Japan ................................ 2-105748

[51] Int. Cl.⁵ .............................................. G01N 3/10
[52] U.S. Cl. ................................................... 73/825
[58] Field of Search ..................... 73/12, 818–823, 73/825–827, 831–834, 837, 857, 49.7; 269/22

[56] References Cited

U.S. PATENT DOCUMENTS

| | | | |
|---|---|---|---|
| Re. 31,993 | 10/1985 | Wesch, Jr. ........................... | 73/49.5 |
| 3,616,685 | 11/1971 | Strom .................................. | 73/819 |
| 3,628,379 | 12/1971 | Babunovic .......................... | 73/818 |
| 3,832,892 | 9/1974 | Bohl .................................... | 73/818 |
| 3,835,698 | 9/1974 | Zappia ................................. | 73/825 |
| 3,955,408 | 5/1976 | Northup . | |
| 4,923,655 | 5/1990 | Oshima et al. . | |
| 4,965,107 | 10/1990 | Oshima et al. . | |
| 5,063,779 | 11/1991 | Landry et al. ...................... | 73/633 |
| 5,197,335 | 3/1993 | Yamada et al. .................... | 73/825 |

OTHER PUBLICATIONS

Patents Abstracts of Japan, vol. 8, No. 248 (P-313) (1685) Nov. 14, 1984 and JP-59 120 936 (Yamamura Glass) Jul. 12, 1984.

*Primary Examiner*—Robert Raevis
*Attorney, Agent, or Firm*—Parkhurst, Wendel & Rossi

[57] ABSTRACT

A bottom strength-inspecting apparatus for bottom-closed hollow pipes is disclosed. This apparatus includes an air chuck 2 for holding an outer peripheral surface of the bottom-closed hollow pipe W, and a pressing elements coaxially provided with the air such an elastic pressing element 8 adapted to contact a bottom surface 9 of the bottom-closed hollow pipe W from an axially outer side of the hollow pipe and press the bottom surface by given forces.

7 Claims, 5 Drawing Sheets

FIG._1A
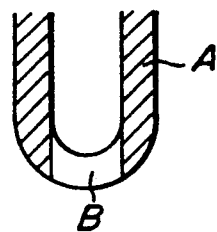
FIG._1B
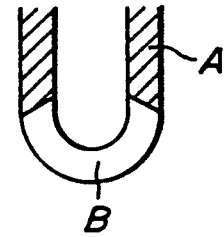
FIG._1C
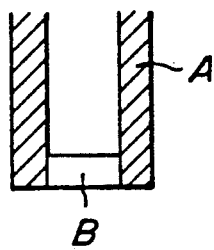
FIG._1D
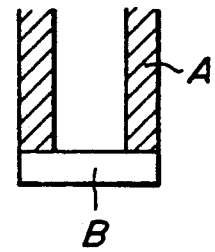
FIG._1E
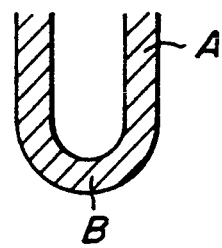

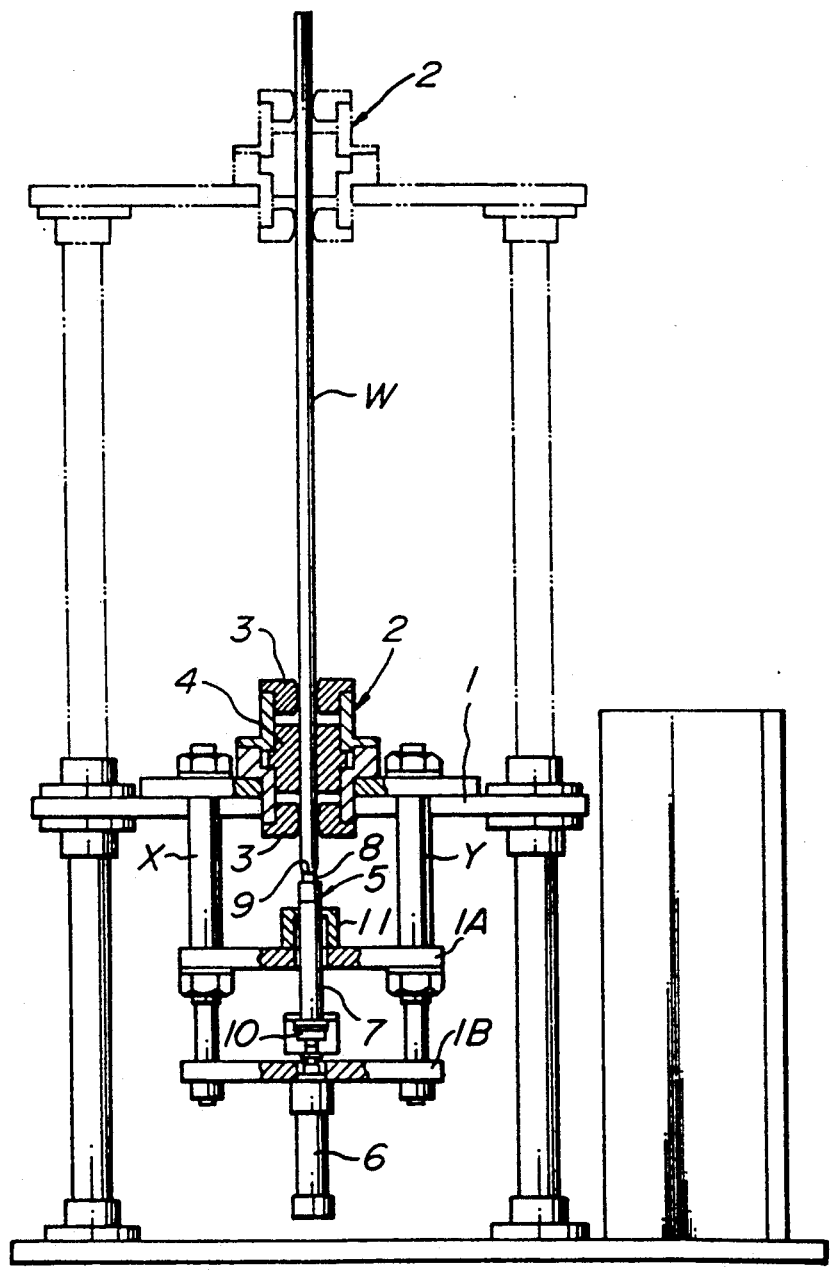
FIG_2

FIG_3
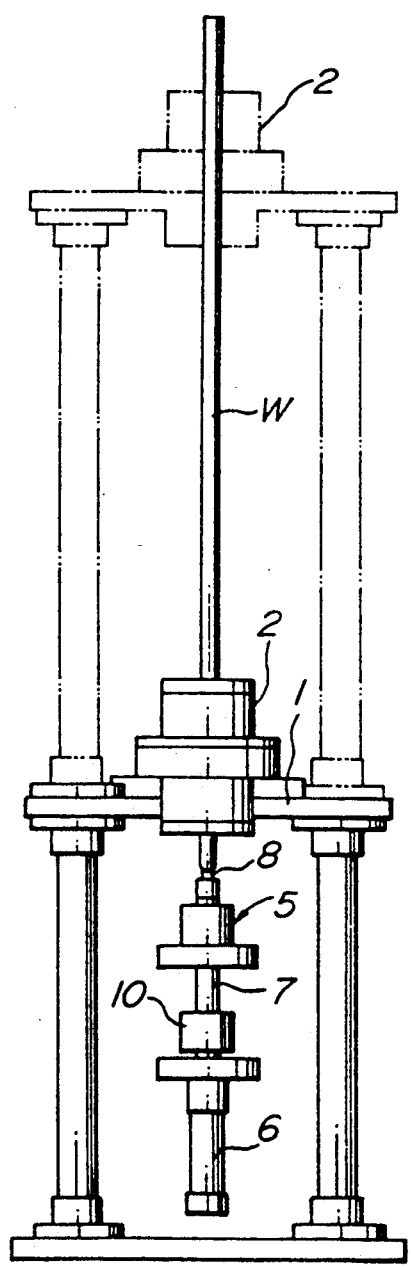
FIG_4
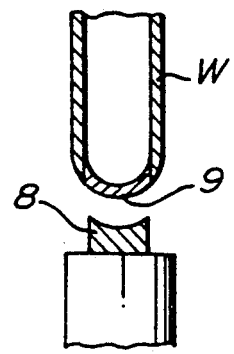

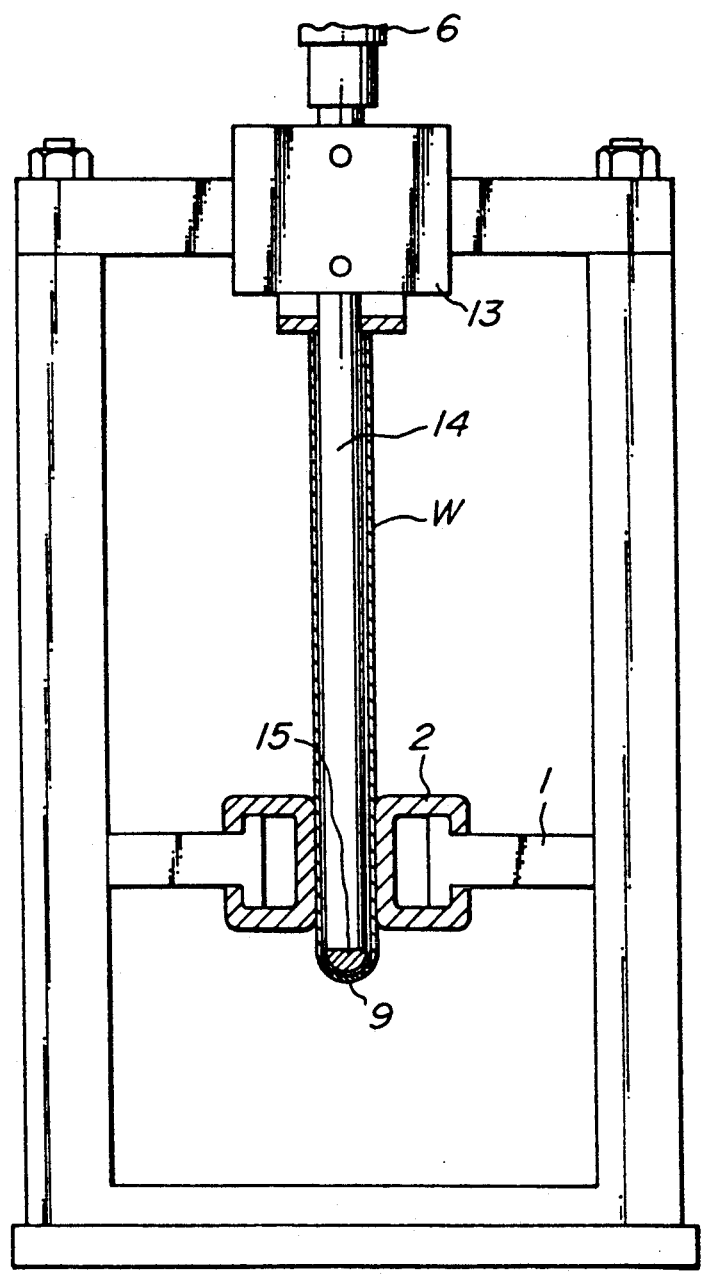
FIG_6 ically shown in FIG. 1E can be also measured according to the present invention.

APPARATUS FOR INSPECTING MECHANICAL STRENGTH OF BOTTOM PORTIONS OF BOTTOM-CLOSED HOLLOW PIPES

This is a continuation of application Ser. No. 07/685,144 filed Apr. 15, 1991, now U.S. Pat. No. 5,197,335.

BACKGROUND OF THE INVENTION

1. Field of the Invention

The present invention relates to an apparatus for inspecting mechanical strength of bottom portions of bottom-closed hollow pipes. For example, this apparatus may be used to inspect mechanical strength of bottom portions of bottom-closed hollow pipes made of zirconia and having the bottoms closed with the same material at one end.

2. Related Art Statement

Although the above ceramic bottom-closed hollow pipe are used, for example, as constituent members for cells, no bottom portion strength-inspecting apparatuses have been formerly known which could accurately inspect strength of the bottom portion of a bottom-closed hollow pipe of this type. Strength of closed hollow pipes have been inspected by applying pressure is applied inside the hollow pipe. However, it is difficult to inspect the strength of the bottom portion, because when high pressure is applied to the interior of the slender bottom-closed hollow pipe, a side wall is first broken. However when such slender bottom-closed hollow pipes are used as constituent parts for fuel cells, they are often broken due to lack in strength at their bottom portions thereby posing a practical problem.

SUMMARY OF THE INVENTION

The present invention solves the above-mentioned problems possessed by the above prior art, and to provides an apparatus for inspecting mechanical strength of bottom portions of slender bottom-closed hollow pipes, which enables ready and accurate inspection of the mechanical strength of the bottom portions of the slender bottom-closed hollow pipes. The term "mechanical strength" used in the specification and claims is intended to mean the following.

The mechanical strength includes both mechanical strength of a bottom portion and bonding strength between a peripheral wall portion and the bottom portion in the case of a one end-closed pipe. If the bonding strength is smaller than the mechanical strength, the former is measured. On the other hand, if the bonding strength is greater than the mechanical strength, the latter is measured.

In FIGS. 1A through 1E, specific forms of the bottom-closed hollow pipes are shown by way of example. In these figures, A and B denote a peripheral wall portion and a bottom portion of the bottom-closed hollow pipes, respectively. In FIGS. 1A through 1D, the bottom portion is bonded to an end portion of the peripheral wall portion with an appropriate bonding agent. The present invention is applicable not only to the bonded type bottom-closed hollow pipes as shown in FIGS. 1A through 1D but also to an integral type as shown in FIG. 1E. In the hollow pipe shown in FIG. 1E, a bottom portion B is not bonded to a peripheral wall portion A, but the former is simultaneously and integrally formed with the formation of the peripheral wall portion, for example, by a casting process. The mechanical strength of the bottom portion B of the bottom-closed hollow pipe as shown in FIG. 1E can be also measured according to the present invention.

A first aspect of the present invention is characterized in that the inspecting apparatus includes an air chuck for holding the outer peripheral surface of the bottom-closed hollow pipe sealed at the bottom portion, and a pressing means provided coaxially with the air chuck, wherein the pressing means is provided with a elastic pressing element which is to contact the outer surface of the bottom portion of the bottom-closed hollow pipe from an outer side thereof and to axially press the outer surface of the bottom portion.

A second aspect of the present invention is characterized in that the inspecting apparatus includes an air chuck for holding the outer peripheral surface of the bottom-closed hollow pipe sealed at the bottom portion, and a pressing means provided coaxially with the air chuck, wherein the pressing means is provided with a pressing rod for passing into of the bottom-closed hollow pipe, and for reaching and pressing the bottom surface of the hollow pipe through an elastic pressing element attached to the tip of the pressing rod.

In the inspecting apparatus according to the present invention, whether adhesion strength of the bottom portion of the bottom-closed slender hollow pipe is acceptable can be accurately determined by applying given forces to the bottom portion of the hollow pipe held by the air chuck by means of the elastic pressing element from the inner surface or the outer surface of the bottom portion in the axial direction of the hollow pipe.

These and other objects, features and advantages of the invention will be appreciated upon reading of the following description of the invention when taken in conjunction with the attached drawings, with the understanding that some modifications, variations and changes of the same could be made by the skilled person in the art to which the invention pertains without departing from the spirit of the claims or the scope of claims appended hereto.

BRIEF DESCRIPTION OF THE DRAWINGS

For a better understanding of the invention, reference is made to the attached drawings, wherein:

FIGS. 1A through 1E are partially sectional views of bottom-closed hollow pipes of which mechanical strength is to be measured by the apparatus of the present invention;

FIG. 2 is a partially sectional view of an embodiment according to the first aspect of the present invention;

FIGS. 3 and 4 are a side view and an enlarged sectional view of a principal portion of FIG. 2, respectively;

FIG. 6 is a partially sectional view of an embodiment according to the second aspect of the present invention.

DETAILED DESCRIPTION OF THE INVENTION

Figure 5:
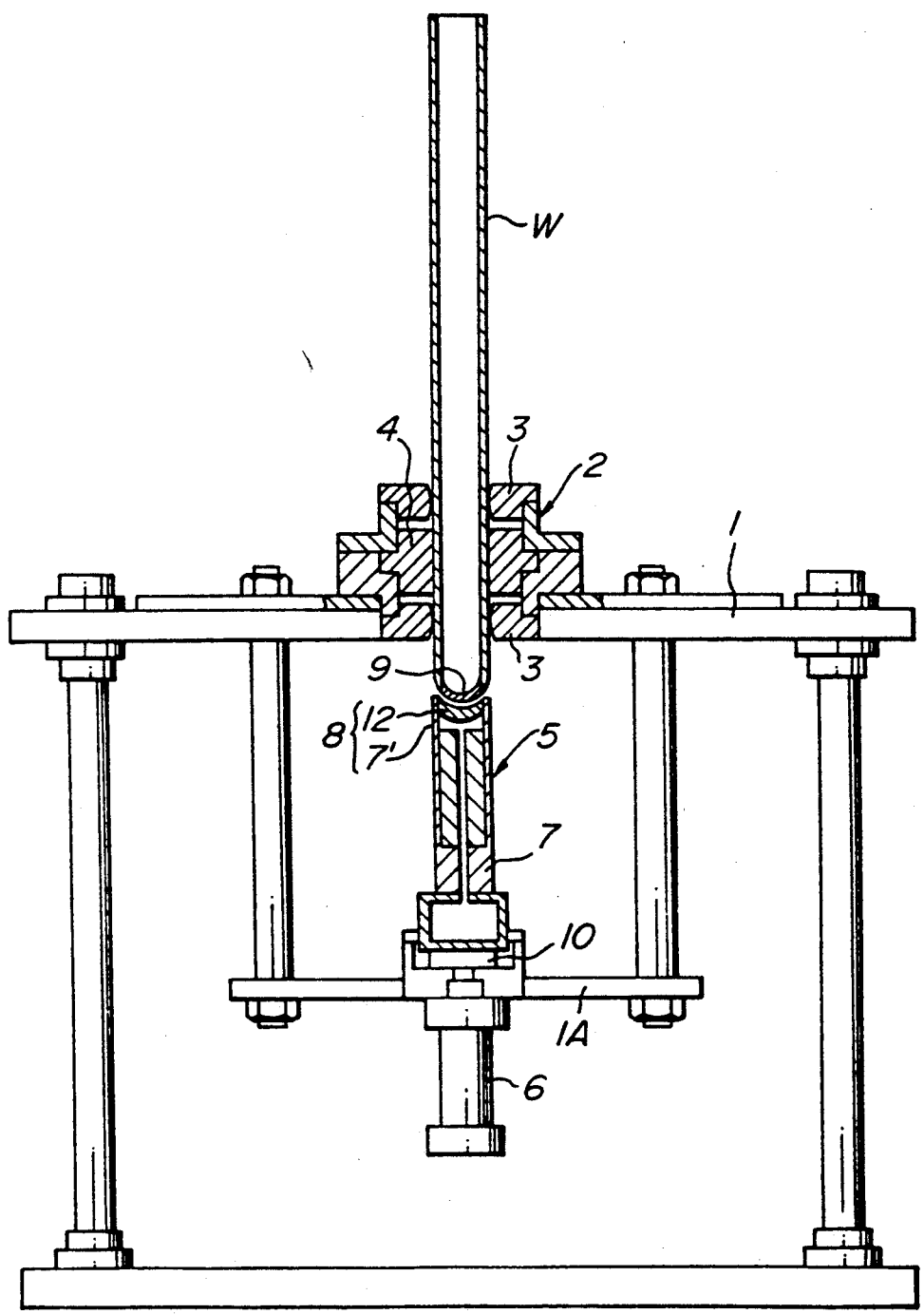
FIG. 5 is a partially sectional view of another embodiment according to the first aspect of the present invention.

The present invention will be explained in more detail with reference to the embodiments shown in the attached drawings.

In FIGS. 2 and 3, a reference numeral 1 is a base, and an air chuck 2 is vertically arranged in a central hole of the base, for supporting the outer peripheral surface of a bottom-closed hollow pipe W. The air chuck includes guide members 3, 3 at upper and lower portions, and a ring-shaped elastic member 4 is arranged in the central portion of a frame of the air chuck. After the hollow pipe is passed through a central hole of the elastic member 4, the elastic member is radially inwardly expanded by air pressure to hold the outer peripheral surface of the bottom-closed hollow cylinder W. Thus, the air chuck can fixedly hold the bottom-closed hollow pipe W in the state that the pipe W is well aligned with the air chuck. If the holding forces are insufficient, as shown in FIGS. 2 and 3 by imaginary lines, another air chuck 2 may be provided above the air chuck 2, through supporting poles and a base at upper ends of the poles.

A reference numeral 5 is a pressing means coaxially arranged under the air chuck 2. In this embodiment, the pressing means 5 includes an air cylinder 6 arranged vertically under the base 1, a pressing rod 7, and an elastic pressing element 8, made of hard rubber, for example attached to the upper tip of the pressing rod 7. That is, rods X and Y are extended downwardly from the base 1, while upper ends of the rods are fixed to the base by bolts. The rods X and Y penetrate bases 1A and 1B under the base 1. The bases 1A and 1B are slidably held through the rods X and Y by means of bolts. The air cylinder 6 is fixed to the under face of the base 1B, and a plunger of the air cylinder 6 is passed through a central hole of the base 1B, and butted or fixed to the under face of the load cell 10 positioned above the base 1B. The lower end of the pressing rod 7 is placed or fixed onto the upper portion of the load cell 10, and the rod 7 passes a central hole provided in the base 1A. A bearing 11 is located on the base 1A. The pressing rod 7 is aligned with the bottom-closed hollow pipe held by the air chuck by means of the upper end of the bearing 11 and the load cell 10. As shown in FIG. 4, the elastic pressing element 8 is adapted to contact and press only a sealed bottom surface 9 of the bottom-closed hollow pipe W from the exterior side. The pressing element 8 has an upper surface curved to conform with the outer profile of the bottom-closed hollow pipe W. By so constructing, local concentration of loads upon the bottom surface 9 can be prevented, and alignment between the bottom-closed hollow pipe and the pressing element can be readily effected. Further, a load cell 10 is interposed between the air cylinder 6 and the pressing rod 7, so that the inspecting means can accurately detect pressing forces at every moment. The bearing 11 which is vertically movably supports the pressing rod 7, and receives the pressing rod 7 at an upper end only. Thereby, the bearing 11 prevents slanting of the bottom-closed hollow pipe W in cooperation with the load cell.

FIG. 5 illustrates a second embodiment in which an elastic pressing element 8 has such a structure that the pressing element 8 is expanded with fluid pressure to be deformed to conform with the configuration of the bottom surface 9 of the bottom-closed hollow pipe W. That is, the elastic pressing element 8 is an elastic rubber member 12 attached to an interior end of a cylindrical guide 7' made of stainless steel or the like and attached to or extended from the upper end of the pressing rod 7. When fluid pressure such as oil pressure, hydraulic pressure, pneumatic pressure or the like is applied to the cylindrical guide 7' through the pressing rod 7, the elastic rubber 12 expands so that the elastic pressing element may closely adhere to the bottom surface 9 of the bottom-closed hollow pipe W. In this embodiment, the other constituent parts are the same (the base 1A and the bearing 11 are not shown, although they may be omitted), and therefore explanation thereof is omitted.

In order to inspect mechanical strength of the bottom-closed hollow pipe W having the bottom portion sealed by means of the bottom strength-inspecting apparatus according to the first aspect of the present invention, the bottom-closed hollow pipe W is downwardly inserted through the air chuck 2 in an opened state as shown, and the bottom face 9 is placed on the elastic pressing element 8 of the pressing means 5. At that time, the bottom-closed hollow pipe W is aligned with the pressing element 8 by means of the upper and lower guide portions 3, 3 of the air chuck 2 and the elastic pressing element 8. Then, pneumatic pressure is applied to the air chuck 2, and the outer peripheral surface of the bottom-closed hollow pipe W is firmly chucked. By actuating the air cylinder 6, only the bottom surface 9 of the bottom-closed hollow pipe W is pressed. At that time, the pressing forces can be accurately detected by means of the load cell 10. Bottom-closed hollow pipes, which are not broken at the bottom face 9 under application of given forces, are judged acceptable. On the other hand, if bottom-closed hollow pipes W have weak mechanical strength for some reason, their bottom faces 9 will be broken.

As explained above, according to the first aspect of the inspecting apparatus of the present invention, the mechanical strength of the bottom portion of the bottom-closed hollow pipe W can be readily and accurately inspected. In addition, since the elastic pressing element 8 is used, local concentration of load upon the bottom surface 9 can be prevented, and the mechanical strength can be measured, while breakage of the material itself constituting the bottom-closed hollow pipe W can be avoided.

FIG. 6 illustrates an embodiment according to the second aspect of the present invention in which a pressing means 13 is provided above an air chuck 2 arranged in a central hole of a base 1. This pressing means 13 is supported at another base fixed to upper ends of supporting poles to which the base 1 is also fixed. An air cylinder 6 is provided above the pressing means 13 through a load cell. The pressing means 13 is provided with a pressing rod 14 which can reach the inner bottom face 9 of the bottom-closed hollow pipe W. The pressing rod 14 is provided with an elastic pressing element 15 at its tip, and the elastic pressing element 15 pushes the bottom surface of the hollow pipe W from the inside. The construction of the pressing element is the same or similar to that in the first aspect of the present invention. In the embodiment of FIG. 6, hard rubber is used as the elastic pressing element 15, but any material which is deformed by expansion by fluid pressure may be used.

In order that the mechanical strength of the bottom portion of the bottom-closed hollow pipe W having the bottom sealed may be inspected by means of the bottom strength-inspecting apparatus for the bottom-closed hollow pipe according to the second aspect of the present invention, the bottom-closed hollow pipe W is first held by the air chuck 2, the pressing rod 14 is inserted into the interior of the hollow pipe, and the elastic pressing element 15 at its lower end is contacted with the bottom surface 9 of the pipe. The pressing rod 14 is lowered by the air cylinder 6 to press the bottom surface 9 of the pipe from the inside. As a result, if the bottom-closed hollow pipe W has low mechanical strength, the bottom face 9 is broken. Similar to the first aspect of the present invention, bottom-closed hollow pipes which are not broken under application of given forces, are judged acceptable.

As mentioned above, according to the present invention, the mechanical strength of the bottom portion of the slender bottom-closed hollow pipe having the bottom portion formed by sealing the end portion can be readily and accurately inspected from the outside or the inside of the pipe by means of the elastic pressing element. Further, according to the present invention, since the elastic pressing element may easily conform with the configuration of the bottom portion of the bottom-closed hollow pipe is used, the mechanical strength can be accurately inspected, while breakage of the material itself due to local concentration of stresses can be avoided.

Therefore, the present invention can greatly contribute to the industrial development as the bottom strength-inspecting apparatus for the bottom-closed hollow pipes, which apparatus solves the problems possessed by the prior art.

What is claimed is:

1. A bottom strength-inspecting system for bottom-closed hollow pipes, said system comprising an air chuck for holding an outer peripheral surface of the bottom-closed hollow pipe, and a pressing means for contacting and pressing by given forces a bottom surface of the bottom-closed hollow pipe, said pressing means being longitudinally coaxially provided with the air chuck and being longitudinally axially movable with respect to the bottom-closed hollow pipe while said bottom-closed hollow pipe is held longitudinally axially stationary by the air chuck, said pressing means comprising an elastic pressing element.

2. The system of claim 1, further comprising a load cell for detecting the forces by which the pressing means presses the bottom surface of the bottom-closed hollow pipe.

3. The system of claim 1, wherein the pressing means further comprises an air cylinder and a pressing rod having one end fitted to the air cylinder, and wherein the elastic pressing element is attached to the other end of the pressing rod and the air cylinder is adapted to make the elastic pressing element press the bottom surface of the hollow pipe by said given forces.

4. The system of claim 1, wherein the elastic pressing element has a face to conform with a shape of the bottom surface of the bottom-closed hollow pipe.

5. The system of claim 1, wherein the elastic pressing element is deformable to make a face of the elastic element to conform with a shape of the bottom surface of the bottom-closed hollow pipe.

6. The system of claim 1, said pressing means further comprises a pressing rod and a guide cylinder, said guide cylinder being attached to said pressing rod at one end thereof, the elastic pressing element being an elastic rubber member attached to an interior end of the guide cylinder over an entire periphery thereof, and the elastic rubber being adapted to be expanded to make the elastic rubber member closely fit the bottom surface of the bottom-closed hollow pipe when fluid pressure is applied to the elastic rubber member through the pressing rod.

7. The system of claim 1, wherein the elastic pressing element is attached to the pressing means by a pressing rod, said pressing rod being adapted to pass into the interior of the bottom-closed hollow pipe thereby enabling the elastic pressing element to press the bottom face from the axially inner side of the hollow pipe.

* * * * *

UNITED STATES PATENT AND TRADEMARK OFFICE
CERTIFICATE OF CORRECTION

PATENT NO. : 5,287,750

DATED : February 22, 1994

INVENTOR(S) : Yamada et al.

It is certified that error appears in the above-identified patent and that said Letters Patent is hereby corrected as shown below:

On the title page, under [*], line 2, change "2000" to --2010--.

Signed and Sealed this

Twenty-sixth Day of July, 1994

Attest:

BRUCE LEHMAN

*Attesting Officer*  *Commissioner of Patents and Trademarks*